United States Patent
Cawley et al.

(10) Patent No.: US 8,882,807 B2
(45) Date of Patent: Nov. 11, 2014

(54) MINIMALLY INVASIVE SURGERY PEDICLE SCREW SYSTEM

(75) Inventors: Trace R. Cawley, Boca Raton, FL (US); Jonathon Doug Payne, Boca Raton, FL (US); Peter Harris, Boca Raton, FL (US)

(73) Assignee: US Spine, Inc., Salt Lake City, UT (US)

( * ) Notice: Subject to any disclaimer, the term of this patent is extended or adjusted under 35 U.S.C. 154(b) by 485 days.

(21) Appl. No.: 12/572,618

(22) Filed: Oct. 2, 2009

(65) Prior Publication Data

US 2010/0087866 A1 Apr. 8, 2010

Related U.S. Application Data

(60) Provisional application No. 61/102,607, filed on Oct. 3, 2008.

(51) Int. Cl.
*A61B 17/70* (2006.01)
*A61B 17/88* (2006.01)

(52) U.S. Cl.
CPC ......... *A61B 17/7085* (2013.01); *A61B 17/7032* (2013.01)
USPC .......................... 606/264; 606/279; 606/86 A

(58) Field of Classification Search
USPC .................... 606/279, 86 A, 99, 104–105, 60, 606/246–278
See application file for complete search history.

(56) References Cited

U.S. PATENT DOCUMENTS

| | | | |
|---|---|---|---|
| 6,530,929 B1 * | 3/2003 | Justis et al. ................. 606/103 |
| 7,476,240 B2 * | 1/2009 | Raymond et al. ............. 606/279 |
| 7,758,584 B2 * | 7/2010 | Bankoski et al. ............. 606/104 |
| 7,763,055 B2 * | 7/2010 | Foley ............................ 606/279 |
| 7,794,479 B2 * | 9/2010 | Aferzon ........................ 606/254 |
| 7,824,410 B2 * | 11/2010 | Simonson et al. .......... 606/86 A |
| 7,867,259 B2 * | 1/2011 | Foley et al. .................... 606/279 |
| 7,871,413 B2 * | 1/2011 | Park et al. ................... 606/86 R |
| 7,918,878 B2 * | 4/2011 | Songer et al. ................. 606/279 |
| 7,947,046 B2 * | 5/2011 | Justis et al. .................. 606/86 A |
| 7,993,344 B2 * | 8/2011 | Pond et al. ................... 606/86 A |
| 2005/0085813 A1 * | 4/2005 | Spitler et al. .................... 606/61 |
| 2005/0192589 A1 * | 9/2005 | Raymond et al. ............... 606/99 |
| 2005/0215999 A1 * | 9/2005 | Birkmeyer et al. ............. 606/61 |
| 2005/0234449 A1 * | 10/2005 | Aferzon .......................... 606/61 |
| 2006/0025768 A1 * | 2/2006 | Iott et al. ......................... 606/61 |
| 2006/0030839 A1 * | 2/2006 | Park et al. ........................ 606/1 |
| 2006/0036244 A1 * | 2/2006 | Spitler et al. .................... 606/61 |
| 2006/0195088 A1 * | 8/2006 | Sacher et al. .................... 606/61 |
| 2006/0247630 A1 * | 11/2006 | Iott et al. ......................... 606/61 |
| 2006/0271050 A1 * | 11/2006 | Piza Vallespir ................ 606/61 |
| 2007/0185491 A1 * | 8/2007 | Foley et al. ...................... 606/61 |
| 2007/0198015 A1 * | 8/2007 | Foley et al. ...................... 606/61 |

(Continued)

*Primary Examiner* — Ellen C Hammond
*Assistant Examiner* — Jacqueline Johanas
(74) *Attorney, Agent, or Firm* — Phillips Ryther & Winchester; Matthew D. Thayne

(57) ABSTRACT

The present invention provides a minimally invasive surgery pedicle screw system, including: a plurality of slotted guides that are selectively inserted through one or more surgical incisions; a plurality of pedicle screws selectively coupled to the plurality of slotted guides that are selectively secured to one or more bony anatomical structures; a pendulum mechanism selectively translatably and pivotably coupled to one of the plurality of slotted guides; and a connecting rod selectively translatably and pivotably coupled to one of the plurality of slotted guides; wherein the pendulum mechanism is selectively coupled to the connecting rod. The connecting rod is selectively secured to one or more of the plurality of pedicle screws.

24 Claims, 3 Drawing Sheets

(56) References Cited

U.S. PATENT DOCUMENTS

| | | | |
|---|---|---|---|
| 2007/0270842 A1* | 11/2007 | Bankoski et al. | 606/61 |
| 2008/0039840 A1* | 2/2008 | Songer et al. | 606/61 |
| 2008/0161857 A1* | 7/2008 | Hestad et al. | 606/264 |
| 2009/0171391 A1* | 7/2009 | Hutton et al. | 606/246 |
| 2010/0114182 A1* | 5/2010 | Wilcox et al. | 606/86 A |

* cited by examiner

MINIMALLY INVASIVE SURGERY PEDICLE SCREW SYSTEM

CROSS-REFERENCE TO RELATED APPLICATION(S)

The present non-provisional patent application/patent claims the benefit of priority of U.S. Provisional Patent Application No. 61/102,607, filed on Oct. 3, 2008, and entitled "MINIMALLY INVASIVE SURGERY PEDICLE SCREW SYSTEM," the contents of which are incorporated in full by reference herein.

FIELD OF THE INVENTION

The present invention relates generally to a minimally invasive surgery (MIS) pedicle screw system including a plurality of pedicle screws and one or more connecting rods for stabilizing/immobilizing adjacent vertebrae of the spine in support of a spinal fusion procedure or the like. The present invention also relates generally to a MIS pedicle screw system including a plurality of slotted guides and an associated pendulum mechanism for placing/securing the one or more connecting rods in the heads of the plurality of pedicle screws. The MIS pedicle screw system of the present invention operates with minimal incision requirements and minimal tissue disruption.

BACKGROUND OF THE INVENTION

When confronted with various spinal diseases and injuries, it is often desirable for a spinal surgeon to perform an interbody fusion or the like, whereby adjacent vertebrae are fused together using a bone graft and/or an implantable device, or otherwise immobilize a portion of the spine of a patient. Typically, in the interbody fusion case, the adjacent vertebrae are immobilized while the bone graft is allowed to "take," for example, using a conventional pedicle screw system, a plate system, or the like. Such a pedicle screw system consists of a plurality of pedicle screws that are anchored to adjacent levels of the spine and connected with stabilizing rods or the like. Such a plate system consists of a plate that is anchored to adjacent levels of the spine and, optionally, connected to the implantable device. Another attractive option when treating various spinal diseases and injuries is to immobilize the associated facet joint(s) using one or more facet bolts or the like. In order to accomplish this, the superior and inferior facets to be joined must be aligned and securely held during drilling and bolt placement, for example. It is also desirable that they are compressed either before or during drilling and bolt placement. This can be a tricky process, which is never desirable during a surgical procedure.

What are still needed in the art are simplified MIS systems and methods for placing a plurality of pedicle screws and securing stabilizing rods or the like to them. Preferably, these systems and methods would have minimal incision requirements and cause minimal tissue disruption, such that quick healing and recovery may be promoted.

BRIEF SUMMARY OF THE INVENTION

In one exemplary embodiment, the present invention provides a minimally invasive surgery pedicle screw system, including: a plurality of slotted guides that are selectively inserted through one or more surgical incisions; a plurality of pedicle screws selectively coupled to the plurality of slotted guides that are selectively secured to one or more bony anatomical structures; a pendulum mechanism selectively translatably and pivotably coupled to one of the plurality of slotted guides; and a connecting rod selectively translatably and pivotably coupled to one of the plurality of slotted guides; wherein the pendulum mechanism is selectively coupled to the connecting rod. The connecting rod is selectively secured to one or more of the plurality of pedicle screws.

In another exemplary embodiment, the present invention provides a minimally invasive surgery pedicle screw method, including: providing a plurality of slotted guides that are selectively inserted through one or more surgical incisions; providing a plurality of pedicle screws selectively coupled to the plurality of slotted guides that are selectively secured to one or more bony anatomical structures; providing a pendulum mechanism selectively translatably and pivotably coupled to one of the plurality of slotted guides; and providing a connecting rod selectively translatably and pivotably coupled to one of the plurality of slotted guides; wherein the pendulum mechanism is selectively coupled to the connecting rod. The connecting rod is selectively secured to one or more of the plurality of pedicle screws.

In a further exemplary embodiment, the present invention provides a minimally invasive surgery pedicle screw system, including: a plurality of slotted guides that are selectively inserted through one or more surgical incisions; a plurality of pedicle screws selectively coupled to the plurality of slotted guides that are selectively secured to one or more bony anatomical structures; a pendulum mechanism selectively translatably and pivotably coupled to one of the plurality of slotted guides; and a rack and pinion perforation assembly selectively translatably and pivotably coupled to one of the plurality of slotted guides; wherein the pendulum mechanism is selectively coupled to the rack and pinion perforation assembly.

BRIEF DESCRIPTION OF THE DRAWINGS

The present invention is illustrated and described herein with reference to the various drawings, in which like reference numbers are used to denote like system components/method steps, as appropriate, and in which.

DETAILED DESCRIPTION OF THE INVENTION

Figure 1:
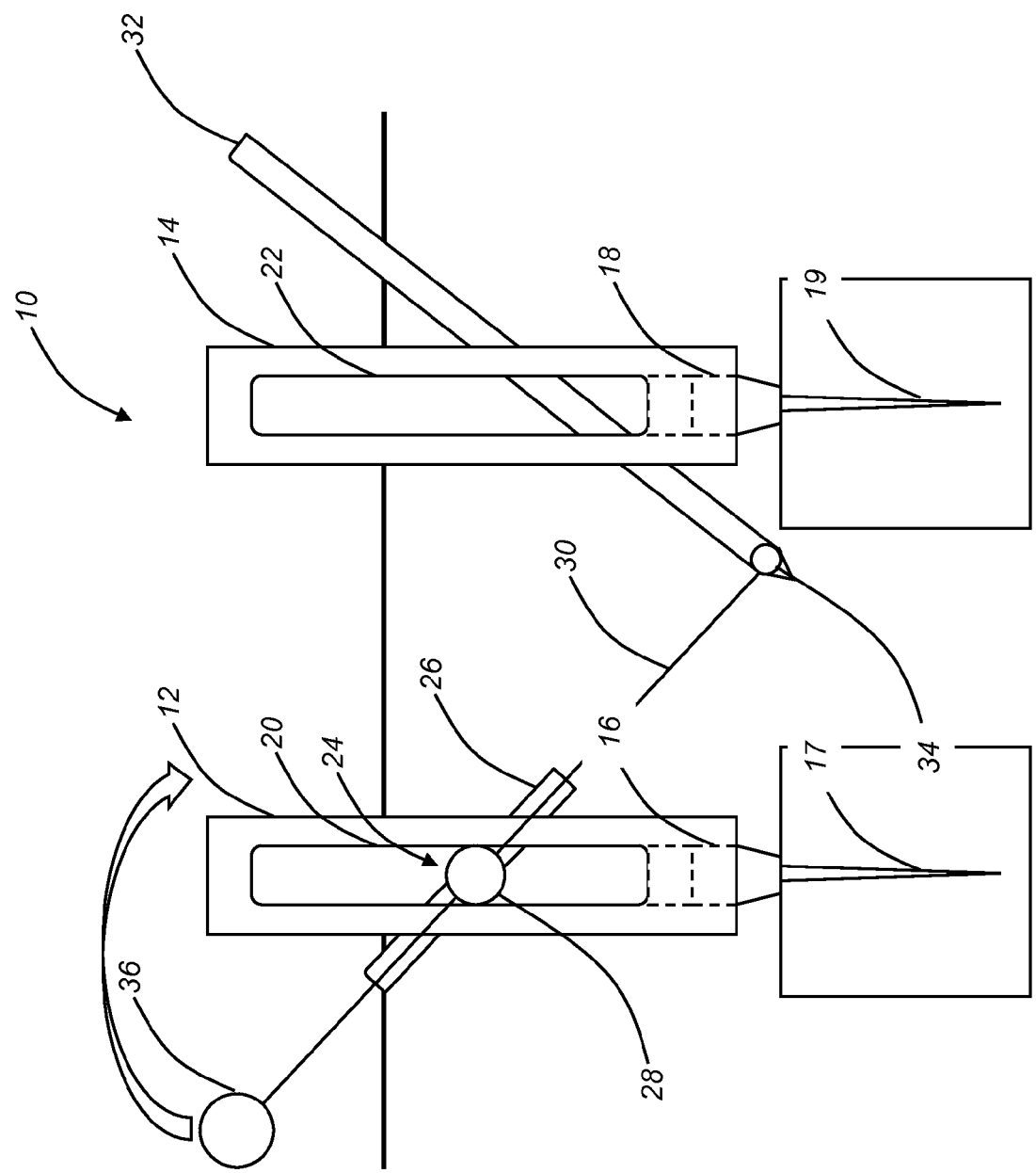
FIG. 1 is a schematic diagram illustrating one exemplary embodiment of the MIS pedicle screw system of the present invention in a partially deployed state.
Figure 2:
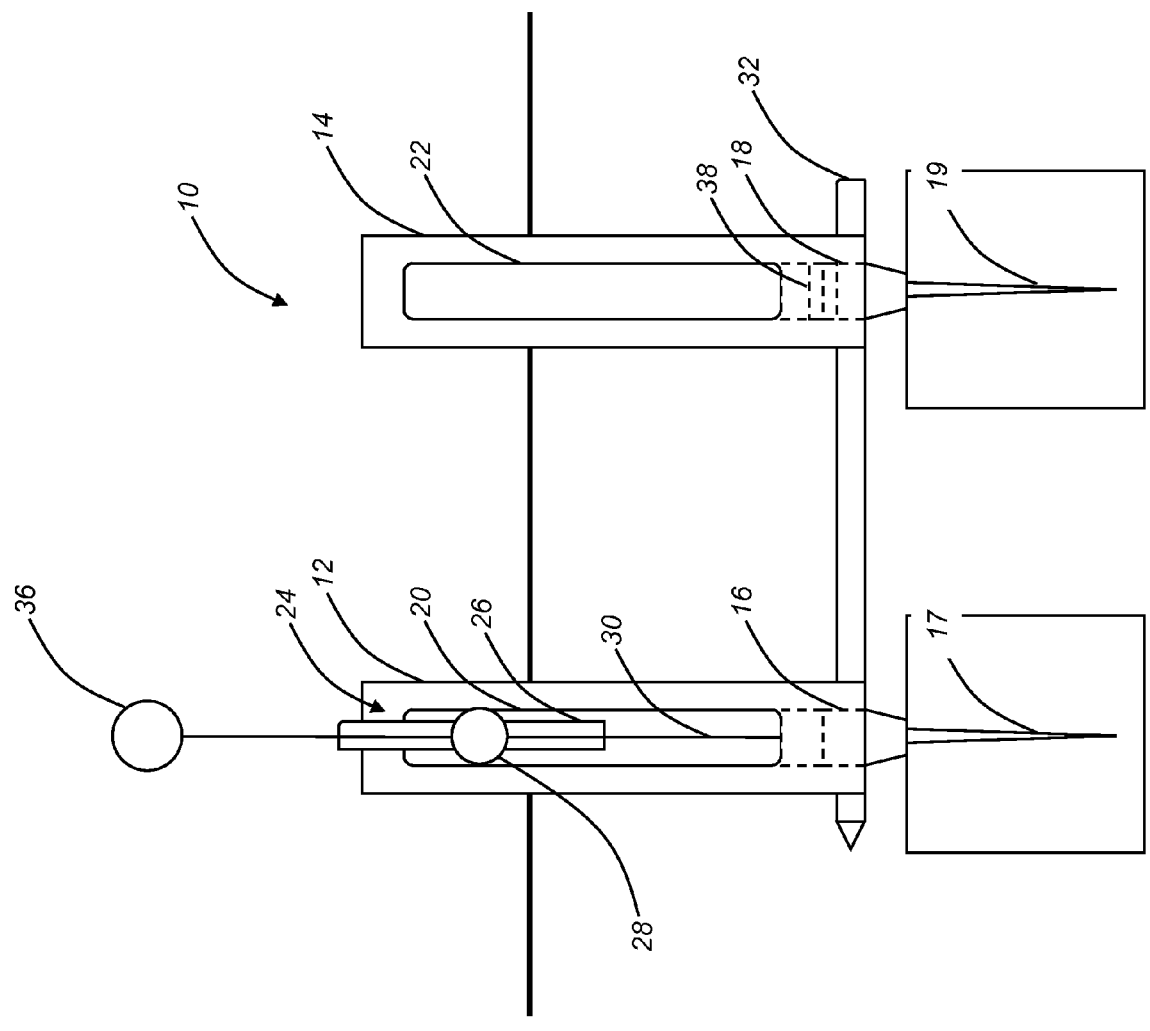
FIG. 2 is a schematic diagram illustrating the MIS pedicle screw system of FIG. 1 in a fully deployed state.

Referring to FIGS. 1 and 2, in one exemplary embodiment, the MIS pedicle screw system 10 of the present invention includes a plurality of slotted guides 12, 14 that are inserted through small incisions in the skin and musculature proximate to the bony structures (i.e. pedicles) of adjacent vertebrae of the spine of a patient. Each of the slotted guides 12, 14 is an elongate structure and is configured to securely receive the head 16, 18 of a pedicle screw 17, 19, such that the slotted guides 12, 14 may be used to drive the pedicle screws 17, 19 into the adjacent pedicles. Preferably, each of the slotted guides 12, 14 is a substantially hollow structure defining a track 20, 22 along its major axis that is configured to receive another structure, as described in greater detail herein below.

The first slotted guide 12 is configured to receive a pendulum mechanism 24 that includes a body portion 26, a pivot structure 28 attached to or integrally formed with the body portion 26, and an elongate portion 30. The elongate portion 30 of the pendulum mechanism 24 may be manufactured from any suitable flexible, semi-rigid, or rigid material. The second slotted guide 14 is configured to receive a connecting rod 32 that also, optionally, includes a pivot structure (not illustrated) attached to or integrally formed with the connecting rod 32. The connecting rod 32 may also be substantially flexible, semi-rigid, or rigid. In operation, the elongate portion 30 of the pendulum mechanism 24 is selectively connected to the connecting rod 32 at an attachment point 34 located at one end of the connecting rod 32.

Referring now specifically to FIG. 1, in operation, the elongate portion 30 of the pendulum mechanism 24 is selectively connected to the connecting rod 32 at the attachment point 34 located at one end of the connecting rod 32. The elongate portion 30 is then pulled upwards through the first slotted guide 12 and pivoted via an associated handle 36 attached to the elongate portion 30. This action causes the pivot structure 28 attached to or integrally formed with the body portion 26 of the pendulum mechanism 24 to translate upwards within the first track 20, as well as to pivot. Accordingly, the first slotted guide 12 includes an elongate opening (not illustrated) along each side through which the body portion 26 and elongate portion 30 of the pendulum mechanism 24 protrude. Because the elongate portion 30 of the pendulum mechanism 24 is connected to the connecting rod 32 at the attachment point 34 located at one end of the connecting rod 32, this action causes the pivot structure (not illustrated) attached to or integrally formed with the connecting rod 32 to translate downwards within the second track 22, as well as to pivot. Accordingly, the second slotted guide 14 includes an elongate opening (not illustrated) along each side through which the connecting rod 32 protrudes.

Referring now specifically to FIG. 2, the connecting rod 32 is eventually drawn into place within the heads 16, 18 of the pedicle screws 17, 19. At this point, a threaded set screw 38 or the like is disposed through the second slotted guide 14 and secured to lock the connecting rod 32 in place relative to the second pedicle screw 19. Optionally, a threaded set screw (not illustrated) or the like is disposed through the first slotted guide 12 and secured to lock the connecting rod 32 in place relative to the first pedicle screw 17. At this point, the pendulum mechanism 24 is withdrawn from the first slotted guide 12, and both slotted guides 12, 14 are disengaged from their respective pedicle screws 17, 19 and removed from the surgical site, which is subsequently closed.

It should be noted that either single or multi-level procedures may be performed using the systems and methods of the present invention.

Figure 3:
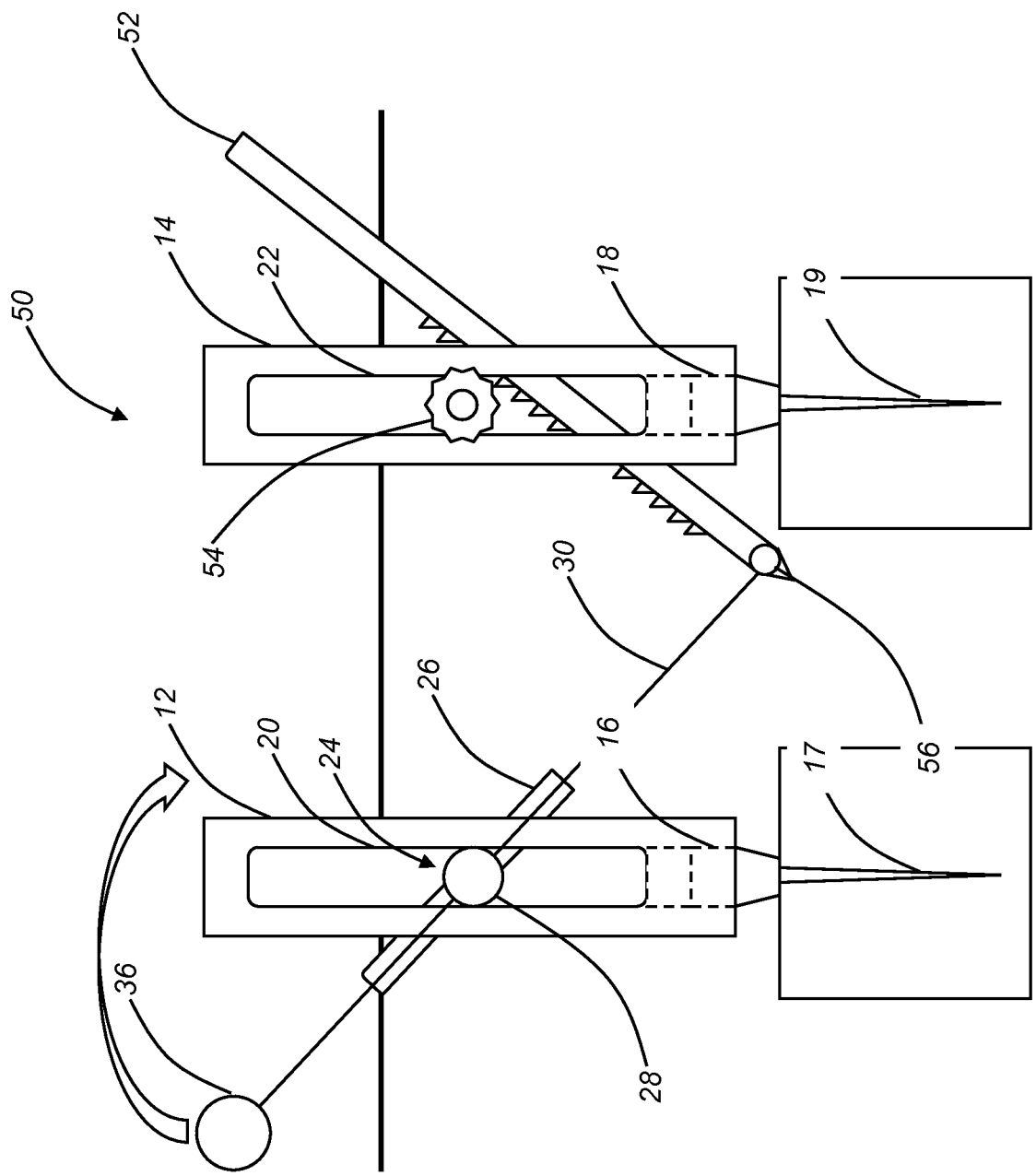
FIG. 3 is a schematic diagram illustrating another exemplary embodiment of the MIS pedicle screw system of the present invention in a partially deployed state, specifically a rack and pinion fascia perforator embodiment.

Referring to FIG. 3, in another exemplary embodiment, the MIS pedicle screw system 50 of the present invention again includes a plurality of slotted guides 12, 14 that are inserted through small incisions in the skin and musculature proximate to the bony structures (i.e. pedicles) of adjacent vertebrae of the spine of a patient. Each of the slotted guides 12, 14 is configured to securely receive the head 16, 18 of a pedicle screw 17, 19, such that the slotted guides 12, 14 may be used to drive the pedicle screws 17, 19 into the adjacent pedicles. Preferably, each of the slotted guides 12, 14 is a substantially hollow structure defining a track 20, 22 along its major axis that is configured to receive another structure, as described in greater detail herein below.

The first slotted guide 12 again is configured to receive a pendulum mechanism 24 that includes a body portion 26, a pivot structure 28 attached to or integrally formed with the body portion 26, and an elongate portion 30. The elongate portion 30 of the pendulum mechanism 24 may be manufactured from any suitable flexible, semi-rigid, or rigid material. The second slotted guide 14 is configured to receive a rack fascia perforator 52 that engages a pinion pivot drive structure 54. In operation, the elongate portion 30 of the pendulum mechanism 24 is selectively connected to the rack fascia perforator 52 at an attachment point 56 located at one end of the rack fascia perforator 52.

In operation, the elongate portion 30 of the pendulum mechanism 24 is selectively connected to the rack fascia perforator 52 at an attachment point 56 located at one end of the rack fascia perforator 52. The elongate portion 30 is then pulled upwards through the first slotted guide 12 and pivoted via an associated handle 36 attached to the elongate portion 30. This action causes the pivot structure 28 attached to or integrally formed with the body portion 26 of the pendulum mechanism 24 to translate upwards within the first track 20, as well as to pivot. Accordingly, the first slotted guide 12 includes an elongate opening (not illustrated) along each side through which the body portion 26 and elongate portion 30 of the pendulum mechanism 24 protrude. Because the elongate portion 30 of the pendulum mechanism 24 is connected to the rack fascia perforator 52 at the attachment point 56 located at one end of the rack fascia perforator 52, this action causes the pinion pivot drive structure 54 to translate downwards within the second track 22, as well as to pivot. Accordingly, the second slotted guide 14 includes an elongate opening (not illustrated) along each side through which the connecting rod 32 protrudes. Optionally, the pinion pivot drive structure 54 drives the motion of the rack fascia perforator 52 and the pendulum mechanism 24.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A minimally invasive surgery pedicle screw system, comprising:
   a plurality of slotted guides that are configured to be selectively inserted through one or more surgical incisions;
   a plurality of pedicle screws configured to be selectively coupled to the plurality of slotted guides, wherein the plurality of pedicle screws are configured to be selectively secured to one or more bony anatomical structures;
   a pendulum mechanism comprising a pivot structure and a body portion extending from the pivot structure, wherein the pivot structure is configured to both translate and pivot within a slot formed within one of the plurality of slotted guides, wherein at least a portion of the pivot structure is confined by and configured to remain entirely within the slot while the pivot structure translates and pivots such that the at least a portion of the pivot structure is prevented from exiting the slot in any direction; and
   a connecting rod configured to be selectively coupled to the pendulum mechanism.

2. The minimally invasive surgery pedicle screw system of claim 1, wherein the connecting rod is configured to be selectively secured to one or more of the plurality of pedicle screws.

3. The minimally invasive surgery pedicle screw system of claim 1, wherein the connecting rod is selectively coupled to the pendulum mechanism such that, as the pivot structure is translated and pivoted within the slot, the connecting rod couples at least two pedicle screws together.

4. The minimally invasive surgery pedicle screw system of claim 3, wherein at least two of the pedicle screws comprise pedicle screw heads, and wherein the connecting rod is selectively coupled to the pendulum mechanism such that, as the pivot structure is translated and pivoted within the slot, the connecting rod couples the at least two pedicle screws together by drawing the connecting rod into the pedicle screw heads.

5. The minimally invasive surgery pedicle screw system of claim 4, wherein the pedicle screw heads are integral with the pedicle screws.

6. The minimally invasive surgery pedicle screw system of claim 1, further comprising a second pendulum mechanism comprising a second pivot structure that is configured to both translate and pivot within a slot formed within a second slotted guide of the plurality of slotted guides.

7. The minimally invasive surgery pedicle screw system of claim 6, wherein the connecting rod is configured to be selectively coupled to the second pendulum mechanism.

8. The minimally invasive surgery pedicle screw system of claim 7, wherein the connecting rod is configured to be selectively coupled to the second pendulum mechanism such that the connecting rod can axially translate within the second slotted guide.

9. The minimally invasive surgery pedicle screw system of claim 6, wherein the second pendulum mechanism comprises a pinion pivot drive structure.

10. The minimally invasive surgery pedicle screw system of claim 1, wherein the pivot structure is configured to both translate and pivot within a slot formed within one of the plurality of slotted guides by applying a pulling force to the pendulum mechanism.

11. The minimally invasive surgery pedicle screw system of claim 10, wherein the pivot structure is configured to both translate and pivot within a slot formed within one of the plurality of slotted guides by applying a pulling force to the pendulum mechanism to couple at least two of the pedicle screws with the connecting rod.

12. A minimally invasive surgery pedicle screw method, comprising:
selectively inserting a plurality of slotted guides through one or more surgical incisions;
selectively coupling a plurality of pedicle screws to the plurality of slotted guides;
securing the plurality of pedicle screws to one or more bony anatomical structures;
coupling a connecting rod to a pendulum mechanism; and
translating and pivoting at least a portion of the pendulum mechanism within a slot formed within one of the plurality of slotted guides by applying a pulling force to the connecting rod to couple at least two of the pedicle screws with the connecting rod, wherein the at least a portion of the pendulum mechanism remains within the slotted guide while the pendulum mechanism translates and pivots.

13. The minimally invasive surgery pedicle screw method of claim 12, further comprising decoupling the connecting rod from the pendulum mechanism.

14. The minimally invasive surgery pedicle screw method of claim 12, wherein the pendulum mechanism comprises a pivot structure, and wherein the pivot structure is positioned to translate and pivot within the slot.

15. The minimally invasive surgery pedicle screw method of claim 12, wherein the translating and pivoting step comprises coupling the at least two pedicle screws together by drawing the connecting rod into screw heads coupled with the pedicle screws.

16. The minimally invasive surgery pedicle screw method of claim 15, wherein the screw heads are integral with the pedicle screws.

17. The minimally invasive surgery pedicle screw method of claim 12, wherein at least a portion of the pendulum mechanism is confined by and remains entirely within the slot while the at least a portion of the pendulum mechanism translates and pivots.

18. The minimally invasive surgery pedicle screw method of claim 17, wherein the at least a portion of the pivot structure is prevented from exiting the slot during the step of translating and pivoting at least a portion of the pendulum mechanism within a slot formed within one of the plurality of slotted guides.

19. A minimally invasive surgery pedicle screw system, comprising:
a plurality of slotted guides that are configured to be selectively inserted through one or more surgical incisions;
a plurality of pedicle screws configured to be selectively coupled to the plurality of slotted guides, wherein the plurality of pedicle screws are configured to be selectively secured to one or more bony anatomical structures;
a pendulum mechanism comprising a pivot structure that is configured to both translate and pivot within a slot formed within a first slotted guide of the plurality of slotted guides;
a pinion pivot drive structure selectively translatably and pivotably coupled to a second slotted guide of the plurality of slotted guides; and
a connecting rod configured to couple at least two of the pedicle screws, wherein the connecting rod comprises a rack fascia perforator configured to engage the pinion pivot drive structure to advance the connecting rod with respect to the pinion pivot drive structure;
wherein the pendulum mechanism is selectively coupled to the pinion pivot drive structure such that selective translation of the pendulum mechanism causes the pinion pivot drive structure to pivot and translate within the second slotted guide as the pivot structure of the pendulum mechanism pivots and translates within the first slotted guide.

20. The minimally invasive surgery pedicle screw system of claim 19, wherein the connecting rod comprises a set of gear teeth configured to engage with the pinion pivot drive structure.

21. The minimally invasive surgery pedicle screw system of claim 19, wherein the connecting rod comprises a set of gear teeth configured to advance the connecting rod into engagement with at least two of the plurality of pedicle screws.

22. The minimally invasive surgery pedicle screw system of claim 19, wherein the pivot structure is configured to both translate and pivot within the slot by applying a pulling force to the pendulum mechanism to couple at least two of the plurality of pedicle screws with the connecting rod.

23. The minimally invasive surgery pedicle screw system of claim 19, wherein at least a portion of the pivot structure is configured such that the at least a portion of the pivot structure is prevented from exiting the slot while the pivot structure translates and pivots within the slot.

24. The minimally invasive surgery pedicle screw system of claim 23, wherein at least a portion of the pinion pivot drive structure is configured such that the at least a portion of the pinion pivot drive structure is prevented from exiting a second slot of the second slotted guide while the pinion pivot drive structure translates and pivots within the second slot.

* * * * *